United States Patent [19]

Krämer et al.

[11] 4,428,949
[45] Jan. 31, 1984

[54] COMBATING FUNGI WITH FLUORINATED 1-AZOLYLBUTANE DERIVATIVES

[75] Inventors: Wolfgang Krämer, Wuppertal; Karl H. Büchel, Burscheid; Jörg Stetter, Wuppertal; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 295,982

[22] Filed: Aug. 25, 1981

[30] Foreign Application Priority Data

Sep. 6, 1980 [DE] Fed. Rep. of Germany ....... 3033592

[51] Int. Cl.³ ................. A01N 43/50; A01N 43/64; C07D 233/60; C07D 249/08
[52] U.S. Cl. .................................. 424/245; 424/269; 424/273 R; 548/101; 548/262; 548/341
[58] Field of Search ............... 548/101, 262, 341; 424/245, 269, 273 R

[56] References Cited

U.S. PATENT DOCUMENTS 4,255,434  3/1981  Kramer et al. ............. 424/273 R

FOREIGN PATENT DOCUMENTS

| 4303 | 3/1979 | European Pat. Off. . |
|---|---|---|
| 6538 | 1/1980 | European Pat. Off. . |
| 9707 | 4/1980 | European Pat. Off. ............ 548/262 |
| 19130 | 11/1980 | European Pat. Off. . |
| 19131 | 11/1980 | European Pat. Off. . |
| 19134 | 11/1980 | European Pat Off. . |
| 19730 | 12/1980 | European Pat. Off. . |
| 25948 | 4/1981 | European Pat. Off. . |
| 25949 | 4/1981 | European Pat. Off. . |
| 26856 | 4/1981 | European Pat. Off. . |
| 2632602 | 1/1978 | Fed. Rep. of Germany . |
| 2632603 | 1/1978 | Fed. Rep. of Germany . |
| 2811916 | 9/1979 | Fed. Rep. of Germany . |
| 2918893 | 11/1980 | Fed. Rep. of Germany ...... 548/341 |
| 2918894 | 11/1980 | Fed. Rep. of Germany ...... 548/262 |
| 7722070 | 2/1978 | France . |

Primary Examiner—Alton D. Rollins
Attorney, Agent, or Firm—Sprung, Horn, Kramer & Woods

[57] ABSTRACT

A 4-fluoro-1-azolyl-1-phenoxy-butan-2-one or -ol of the formula

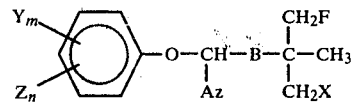

in which
Az is an imidazol-1-yl, 1,2,4-triazol-1-yl or 1,2,4-triazol-4-yl radical,
B is a keto or CH(OH) group,
X is a hydrogen or fluorine atom,
Y is an alkoxy, alkylthio, halogenoalkyl, halogenoalkoxy or halogenoalkylthio radical,
Z is a halogen atom or an alkyl radical,
m is 1, 2 or 3 and
n is 0, 1 or 2, or an addition product thereof with a physiologically acceptable acid or a metal salt, which possesses fungicidal activity.

10 Claims, No Drawings

COMBATING FUNGI WITH FLUORINATED 1-AZOLYLBUTANE DERIVATIVES

The present invention relates to certain new fluorinated 1-azolyl-butane derivatives, to a process for their preparation and to their use as fungicides.

It has already been disclosed that chlorinated and brominated 1-imidazolyl- and -triazolyl-butane derivatives have good fungicidal properties (see our DE-OS (German Published Specification) No. 2,632,602 and U.S. Application Ser. No. 964,215, filed Nov. 27, 1978, now U.S. Pat. No. 4,255,434). However, the action of these compounds is not always completely satisfactory, especially when low amounts and concentrations are applied.

The present invention now provides, as new compounds, the fluorinated 1-azolyl-butane derivatives of the general formula

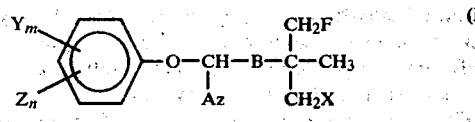

in which
Az represents an imidazol-1-yl, 1,2,4-triazol-1-yl or 1,2,4-triazol-4-yl radical
B represents a keto group or a CH(OH) grouping,
X represents a hydrogen or fluorine atom,
Y represents an alkoxy, alkylthio, halogenoalkyl, halogenoalkoxy or halogenoalkylthio radical,
Z represents a halogen atom or an alkyl radical,
m is 1, 2 or 3 and
n is 0, 1 or 2, and physiologically acceptable acid addition salts and metal salt complexes thereof.

Those compounds of the formula (I) in which B represents the CH(OH) grouping have two asymmetric carbon atoms; they can therefore exist in two geometrically isomer forms (threo-form and erythro-form), which can be obtained in various proportions. In both cases, they are in the form of optical isomers. All the isomers are claimed according to the invention.

According to the present invention we further provide a process for the production of a compound of the present invention, characterized in that a halogenoether-ketone of the general formula

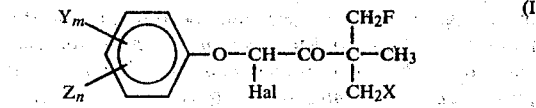

in which
X, Y, Z, n and m have the abovementioned meanings and
Hal represents a halogen atom, preferably a chlorine or bromine atom, is reacted with imidazole or 1,2,4-triazole in the presence of an acid-binding agent and, where appropriate, in the presence of a diluent, and, if a compound of formula (I) in which B represents CH(OH) is required the resulting keto derivative is reduced; and the fluorinated 1-azolyl butane derivative of formula (I) in which B has either of its possible meanings is converted, if desired, into an acid addition salt or metal salt complex thereof.

The new fluorinated 1-azolyl-butane derivatives of the present invention have powerful fungicidal properties. Surprisingly, the compounds according to the invention exhibit a more powerful action than the chlorinated and brominated 1-imidazolyl- and -triazolyl-butane derivatives which are known from the state of the art and are very closely related compounds chemically and from the point of view of their action. The substances according to the invention thus represent an enrichment of the art.

Preferred fluorinated 1-azolyl-butane derivatives according to the present invention are those in which Y represents an alkoxy or alkylthio radical with in each case 1 to 4 carbon atoms, or a halogenoalkyl, halogenoalkoxy or halogenoalkylthio radical with in each case 1 or 2 carbon atoms and 1 to 5 identical or different halogen atoms (such as, in particular, fluorine and chlorine atoms), Z represents a halogen atom or an alkyl radical with 1 to 4 carbon atoms, and Az, B, X, m and n have the meanings given above.

Particularly preferred fluorinated 1-azolyl-butane derivatives of the present invention are those in which Y represents a methoxy, ethoxy, isopropoxy, tert.-butyloxy, methylthio, trifluoromethyl, chlorodifluoromethyl, dichlorofluoromethyl, trichloromethyl, trifluoromethoxy or trifluoromethylthio radical, Z represents a fluorine or chlorine atom or a methyl group, and Az, B, X, m and n have the meanings given above.

The following compounds of the general formula (I) may be mentioned specifically, in addition to the compounds mentioned in the Preparative Examples hereinbelow:

| $Y_m$ | $Z_n$ | B | X | Az |
|---|---|---|---|---|
| 3,5-(CF$_3$)$_2$ | — | CO | F | 1,2,4-Triazol-1-yl |
| 4-SCF$_3$ | — | CO | F | 1,2,4-Triazol-1-yl |
| 4-OCF$_3$ | — | CO | F | 1,2,4-Triazol-1-yl |
| 4-SCF$_3$ | — | CO | F | 1,2,4-Triazol-1-yl |
| 4-SCF$_3$ | 3-CH$_3$ | CO | F | 1,2,4-Triazol-1-yl |
| 4-CF$_3$ | 2-Cl | CO | F | 1,2,4-Triazol-1-yl |
| 4-SCF$_3$ | 2,6-Cl$_2$ | CO | F | 1,2,4-Triazol-1-yl |
| 3,5-(CF$_3$)$_2$ | — | CH(OH) | F | 1,2,4-Triazol-1-yl |
| 4-SCF$_3$ | — | CH(OH) | F | 1,2,4-Triazol-1-yl |
| 4-OCF$_3$ | — | CH(OH) | F | 1,2,4-Triazol-1-yl |
| 4-SCH$_3$ | — | CH(OH) | F | 1,2,4-Triazol-1-yl |
| 4-SCF$_3$ | 3-CH$_3$ | CH(OH) | F | 1,2,4-Triazol-1-yl |
| 4-CF$_3$ | 2-Cl | CH(OH) | F | 1,2,4-Triazol-1-yl |
| 4-SCF$_3$ | 2,6-Cl$_2$ | CH(OH) | F | 1,2,4-Triazol-1-yl |
| 3,5-CF$_3$ | — | CO | H | 1,2,4-Triazol-1-yl |
| 4-SCF$_3$ | — | CO | H | 1,2,4-Triazol-1-yl |
| 4-OCF$_3$ | — | CO | H | 1,2,4-Triazol-1-yl |
| 4-SCH$_3$ | — | CO | H | 1,2,4-Triazol-1-yl |
| 4-SCF$_3$ | 3-CH$_3$ | CO | H | 1,2,4-Triazol-1-yl |
| 4-CF$_3$ | 2-Cl | CO | H | 1,2,4-Triazol-1-yl |
| 4-SCF$_3$ | 2,6-Cl$_2$ | CO | H | 1,2,4-Triazol-1-yl |
| 3,5-(CF$_3$)$_2$ | — | CH(OH) | H | 1,2,4-Triazol-1-yl |
| 4-SCF$_3$ | — | CH(OH) | H | 1,2,4-Triazol-1-yl |
| 4-OCF$_3$ | — | CH(OH) | H | 1,2,4-Triazol-1-yl |
| 4-SCH$_3$ | — | CH(OH) | H | 1,2,4-Triazol-1-yl |
| 4-SCF$_3$ | 3-CH$_3$ | CH(OH) | H | 1,2,4-Triazol-1-yl |
| 4-CF$_3$ | 2-Cl | CH(OH) | H | 1,2,4-Triazol-1-yl |
| 4-SCF$_3$ | 2,6-Cl$_2$ | CH(OH) | H | 1,2,4-Triazol-1-yl |
| 3,5-(CF$_3$)$_2$ | — | CO | F | Imidazol-1-yl |
| 4-SCF$_3$ | — | CO | F | Imidazol-1-yl |
| 4-OCF$_3$ | — | CO | F | Imidazol-1-yl |
| 4-SCH$_3$ | — | CO | F | Imidazol-1-yl |
| 4-SCF$_3$ | 3-CH$_3$ | CO | F | Imidazol-1-yl |

-continued

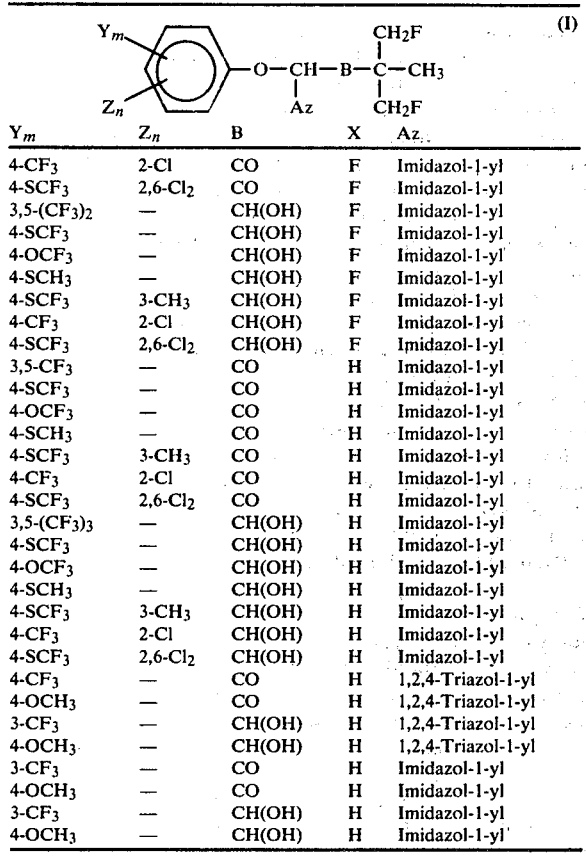

| $Y_m$ | $Z_n$ | B | X | Az |
|---|---|---|---|---|
| 4-CF$_3$ | 2-Cl | CO | F | Imidazol-1-yl |
| 4-SCF$_3$ | 2,6-Cl$_2$ | CO | F | Imidazol-1-yl |
| 3,5-(CF$_3$)$_2$ | — | CH(OH) | F | Imidazol-1-yl |
| 4-SCF$_3$ | — | CH(OH) | F | Imidazol-1-yl |
| 4-OCF$_3$ | — | CH(OH) | F | Imidazol-1-yl |
| 4-SCH$_3$ | — | CH(OH) | F | Imidazol-1-yl |
| 4-SCF$_3$ | 3-CH$_3$ | CH(OH) | F | Imidazol-1-yl |
| 4-CF$_3$ | 2-Cl | CH(OH) | F | Imidazol-1-yl |
| 4-SCF$_3$ | 2,6-Cl$_2$ | CH(OH) | F | Imidazol-1-yl |
| 3,5-CF$_3$ | — | CO | H | Imidazol-1-yl |
| 4-SCF$_3$ | — | CO | H | Imidazol-1-yl |
| 4-OCF$_3$ | — | CO | H | Imidazol-1-yl |
| 4-SCH$_3$ | — | CO | H | Imidazol-1-yl |
| 4-SCF$_3$ | 3-CH$_3$ | CO | H | Imidazol-1-yl |
| 4-CF$_3$ | 2-Cl | CO | H | Imidazol-1-yl |
| 4-SCF$_3$ | 2,6-Cl$_2$ | CO | H | Imidazol-1-yl |
| 3,5-(CF$_3$)$_3$ | — | CH(OH) | H | Imidazol-1-yl |
| 4-SCF$_3$ | — | CH(OH) | H | Imidazol-1-yl |
| 4-OCF$_3$ | — | CH(OH) | H | Imidazol-1-yl |
| 4-SCH$_3$ | — | CH(OH) | H | Imidazol-1-yl |
| 4-SCF$_3$ | 3-CH$_3$ | CH(OH) | H | Imidazol-1-yl |
| 4-CF$_3$ | 2-Cl | CH(OH) | H | Imidazol-1-yl |
| 4-SCF$_3$ | 2,6-Cl$_2$ | CH(OH) | H | Imidazol-1-yl |
| 4-CF$_3$ | — | CO | H | 1,2,4-Triazol-1-yl |
| 4-OCH$_3$ | — | CO | H | 1,2,4-Triazol-1-yl |
| 3-CF$_3$ | — | CH(OH) | H | 1,2,4-Triazol-1-yl |
| 4-OCH$_3$ | — | CH(OH) | H | 1,2,4-Triazol-1-yl |
| 3-CF$_3$ | — | CO | H | Imidazol-1-yl |
| 4-OCH$_3$ | — | CO | H | Imidazol-1-yl |
| 3-CF$_3$ | — | CH(OH) | H | Imidazol-1-yl |
| 4-OCH$_3$ | — | CH(OH) | H | Imidazol-1-yl |

If, for example, 1-bromo-1-(3-trifluoromethylphenoxy)-3,3-dimethyl-4-fluoro-butan-2-one and 1,2,4-triazole are used as starting substances, the course of the reaction according to the present invention is illustrated by the following equation:

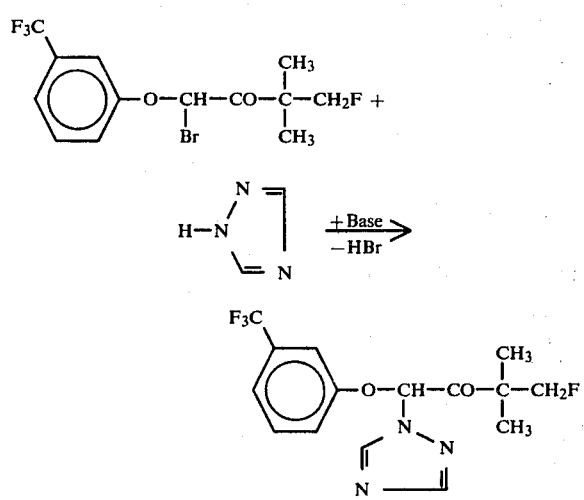

If, for example, 3,3-dimethyl-4-fluoro-1-(1,2,4-triazol-1-yl)-1-(3-trifluoromethylphenoxy)-butan-2-one and sodium borohydride are used as starting substances, the course of the reduction reaction according to the present invention is illustrated by the following equation:

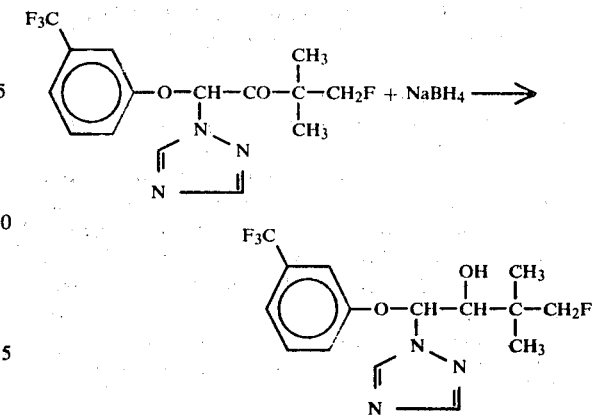

Preferred halogenoether-ketones of formula (II) to be used as starting substances in carrying out the process according to the invention are those in which X, Y, Z, m and n have those meanings which have already been mentioned in connection with the description of the preferred and particularly preferred substances of the formula (I) according to the invention.

The halogenoether-ketones of the formula (II) are novel. However, they can be obtained by known processes (see for example, U.S. Ser. No. 964,215, filed Nov. 27, 1978, now U.S. Pat. No. 4,255,434, supra), for example by reacting known phenols of the general formula

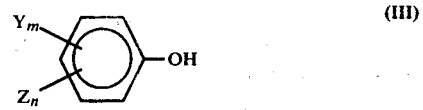

in which Y, Z, m and n have the abovementioned meanings, with a known (see U.S. Ser. No. 77,447, filed Sept. 20, 1979, now U.S. Pat. No. 4,267,381) halogenoketone of the general formula

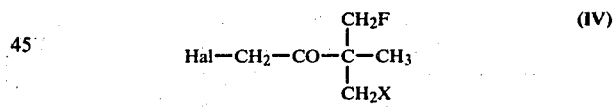

in which Hal and X have the abovementioned meanings. The active hydrogen atom which still remains is then replaced by halogen in the customary manner (see also the preparative examples).

Inert organic solvents are possible diluents for the reaction according to the invention. These solvents include, preferably, ketones (such as diethyl ketone, and in particular acetone and methyl ethyl ketone); nitriles (such as propionitrile, and in particular acetonitrile); alcohols (such as ethanol or isopropanol); ethers (such as tetrahydrofuran or dioxane); benzene; toluene; formamides (such as, in particular, dimethylformamide); and halogenated hydrocarbons.

The reaction according to the invention is carried out in the presence of an acid-binding agent. Any of the inorganic or organic acid-binding agents which can customarily be used may be added, such as alkali metal carbonates (for example sodium carbonate and sodium bicarbonate), lower tertiary alkylamines, cycloalkylamines or aralkylamines (for example triethylamine, N,N-dimethylcyclohexylamine, dicyclohexylamine and N,N-dimethylbenzylamine), pyridine and diazabicyclooctane.

Preferably, an appropriate excess of 1,2,4-triazole or imidazole is used.

The reaction temperatures can be varied within a substantial range. In general, the reaction is carried out at a temperature between 20° C. and 150° C., preferably at a temperature between 60° C. and 120° C. If a solvent is present, it is expedient to carry out the reaction at the boiling point of the particular solvent.

In carrying out the process according to the invention, 2 moles of azole and 1 to 2 moles of acid-binding agent are preferably employed per mole of the compounds of the formula (II). To isolate the compounds of the formula (I), the solvent is distilled off, the residue is taken up in an organic solvent and the mixture is washed with water. The organic phase is dried over sodium sulphate, and freed from the solvent in vacuo. The residue is purified by distillation or recrystallization, or salt formation and recrystallization.

The reduction according to the invention is carried out in the customary manner, such as, for example, by reaction with complex hydrides, where appropriate in the presence of a diluent, or by reaction with aluminum isopropylate in the presence of a diluent.

If complex hydrides are used, polar organic solvents are possible diluents for the reaction according to the invention. These solvents include, preferably, alcohols (such as methanol, ethanol, butanol or isopropanol) and ethers (such as diethyl ether or tetrahydrofuran). The reaction is in general carried out at 0° to 30° C., preferably at 0° to 20° C. For this reaction, generally about 1 mole of a complex hydride (such as sodium borohydride or lithium alanate) is employed per mole of the ketone of the formula (I). To isolate the reduced compounds of the formula (I), the residue is taken up in dilute hydrochloric acid and the mixture is then rendered alkaline and extracted with an organic solvent. Further working up is effected in the customary manner.

If aluminum isopropylate is used, preferred possible diluents for the reaction according to the invention are alcohols (such as isopropanol), or inert hydrocarbons (such as toluene). The reaction temperatures can again be varied within a substantial range; in general, the reaction is carried out at a temperature between 20° C. and 120° C., preferably at a temperature between 50° C. and 100° C. For carrying out the reaction, about 0.3 to 2 moles of aluminum isopropylate are employed per mole of the ketone of the formula (I). To isolate the reduced compounds of the formula (I), the excess solvent is removed in vacuo and the aluminum compounds formed are decomposed with dilute sulphuric acid or sodium hydroxide solution. Further working up is effected in the customary manner.

Any of the physiologically acceptable acids can be used for the preparation of acid addition salts of the compounds of the formula (I). These acids include, preferably, hydrogen halide acids (such as hydrobromic acid, in particular hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid) and sulphonic acids (such as p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable solvent and adding the acid, for example hydrogen chloride, and they can be isolated in a known manner, for example by filtration, and where appropriate purified by washing with an inert organic solvent or by recrystallization.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which are derived from physiological acids. These include, preferably, hydrogen halide acids (such as hydrochloric acid and hydrobromic acid), and furthermore phosphoric acid, nitric acid and sulphuric acid.

The metal salt complexes of the compounds of the formula (I) can be obtained in a simple manner by customary processes, thus, for example, by dissolving the metal salt in alcohol (for example ethanol) and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as powdery mildew of cereal and powdery mildew of barley, and for combating powdery mildew of cucumber (*Erysiphe cichoracearum*) powdery mildew of apple (*Podosphaera leucotricha*) and apple scab (*Fusicladium dendriticum*). It should be emphasised that the substances according to the invention not only display a protective action but also have systemic action. It is thus possible to protect plants from fungal attack if the active compounds are fed to the above-ground parts of the plant via the soil and the roots or via the seed.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquid which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ether, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are generally required at the place of action.

The present invention also provides fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the harvested crop may be improved by the present invention.

PREPARATIVE EXAMPLES

Example 1

(a) 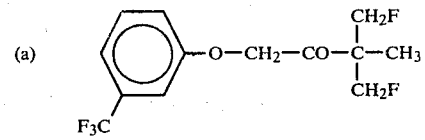

215 g (1 mole) of 3,3-bisfluoromethyl-1-bromobutan-2-one were added dropwise to a stirred mixture of 162 g (1 mole) of 3-trifluoromethylphenol and 180 g (1.3 moles) of powdered potassium carbonate in 1,200 ml of acetone at 20° to 30° C. The mixture was stirred at 50° C. for 6 hours the inorganic salt was filtered off and the filtrate was concentrated. The residue was distilled under a high vacuum. 210 g of 3,3-bisfluoromethyl-1-(3-trifluoromethylphenoxy)-butan-2-one of boiling point 114°–18° C./0.6 mm Hg were obtained.

(b) 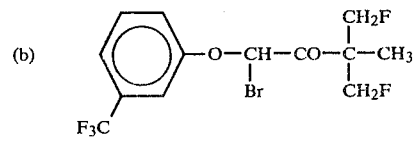

210 g (0.71 mole) of 3,3-bisfluoromethyl-1-(3-trifluoromethyl-phenoxy)-butan-2-one were dissolved in 500 ml of methylene chloride, and 36.1 ml (0.71 mole) of bromine in 40 ml of methylene chloride were added dropwise at 20° to 30° C., while stirring. The mixture was subsequently stirred at 20° C. for 2 hours and was concentrated in vacuo by distilling off the solvent.

The oily residue was distilled under a high vacuum. 235 g of 3,3-bisfluoromethyl-1-bromo-1-(3-trifluoromethylphenoxy)-butan-2-one of boiling point 110°-16° C./0.06 mm Hg were obtained.

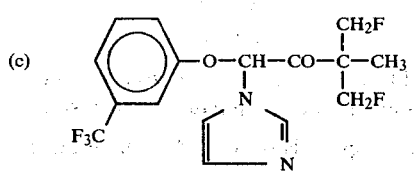

135 g (0.36 mole) of 3,3-bisfluoromethyl-1-bromo-1-(3-trifluoromethyl-phenoxy)-butan-2-one in 400 ml of acetone were added dropwise to 24.5 g (0.36 mole) of imidazole and 55.3 g (0.4 mole) of potassium carbonate in 400 ml of acetone. The mixture was stirred at 50° C. for 6 hours and was then concentrated by distilling off the solvent under a waterpump vacuum. The oily residue was taken up in 800 ml of methylene chloride, the mixture was washed twice with 2,000 ml of water each time, the organic phase was stirred with active charcoal, filtered and dried over sodium sulphate and the solvent was distilled off. The oily residue was distilled under a high vacuum. 63.4 g (48.8% of theory) of 3,3-bisfluoromethyl-1-(imidazol-1-yl)-1-(3-trifluoromethyl-phenoxy)-butan-2-one of boiling point 169°-73° C./0.1 mm Hg were obtained.

Example 2

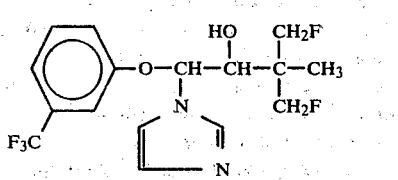

63.7 g (0.176 mole) of 3,3-bisfluoromethyl-1-(imidazol-1-yl)-1-(3-trifluoromethylphenoxy)-butan-2-one (obtained as described in Example 1) were dissolved in 250 ml of methanol, and 3 g (0.08 mole) of sodium borohydride were added in portions. The reaction solution was subsequently stirred for 1 hour and was then adjusted to a pH value of 3 with concentrated hydrochloric acid. After distilling off the solvent in vacuo, water was added to the residue and the mixture was extracted by shaking with methylene chloride. The combined organic phases were dried over sodium sulphate and concentrated in vacuo. 44.5 g (70% of theory) of 3,3-bisfluoromethyl-1-(imidazol-1-yl)-1-(3-trifluoromethylphenoxy)-butan-2-ol of melting point 107°-20° C. were obtained.

Example 3

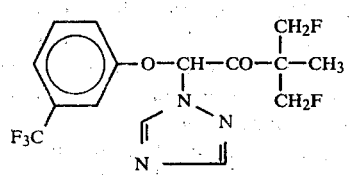

100 g (0.267 mole) of 3,3-bis fluoromethyl-1-bromo-1-(3-trifluoromethylphenoxy)-butan-2-one and 37.2 g (0.54 mole) of 1,2,4-triazole in 600 ml of acetonitrile were heated to 65° C. for 6 hours, while stirring. The solvent was then distilled off under a waterpump vacuum, the residue was taken up in 800 ml of methylene chloride and the mixture was washed twice with 1,000 ml of water each time. The organic phase was dried over sodium sulphate and concentrated. The oily residue was distilled under a high vacuum. 80 g (82.4% of theory) of 3,3-bisfluoromethyl-1-(1,2,4-triazol-1-yl)-1-(3-trifluoromethylphenoxy)-butan-2-one of boiling point 136°-41° C./0.1 mm Hg were obtained.

The following examples of the following general formula

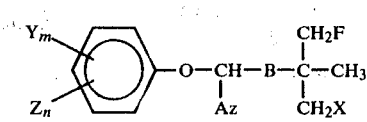

were obtained in a corresponding manner:

| Compound No. | $Y_m$ | $Z_n$ | B | X | Az | Melting point (°C.) or boiling point (°C./mm Hg) |
|---|---|---|---|---|---|---|
| 4 | 4-OCH$_3$ | — | CO | F | -N⟨N=CH-CH=N⟩ | 247-49 (× ½ NDS) |
| 5 | 4-OCH$_3$ | — | CH(OH) | F | -N⟨N=CH-CH=N⟩ | 110-15 |
| 6 | 4-OCH$_3$ | — | CO | F | -N-N⟨=CH-CH=N⟩ | oil |
| 7 | 3-CF$_3$ | — | CH(OH) | F | -N-N⟨=CH-CH=N⟩ | 143-47 (A-form) |
| 8 | 4-OCH$_3$ | — | CH(OH) | F | -N-N⟨=CH-CH=N⟩ | 109-11 (A-form) |
| 9 | 3-CF$_3$ | — | CH(OH) | F | -N-N⟨=CH-CH=N⟩ | 210-215 (× MnCl$_2$) |
| 10 | 4-OCH$_3$ | — | CH(OH) | F | -N⟨N=CH-CH=N⟩ | 200 (× CuCl$_2$) |
| 11 | 3-CF$_3$ | — | CH(OH) | F | -N⟨N=CH-CH=N⟩ | 145-156 (× CuCl$_2$) |

NDS = 1,5-naphthalenedisulphonic acid
A-form = one of the two possible geometric isomers The fungicidal activity of the compounds of this invention is illustrated by the following examples wherein the compounds according to the present invention are each identified by the number (given in brackets) from the preparative examples and table hereinabove.

The known comparison compounds are identified as follows:

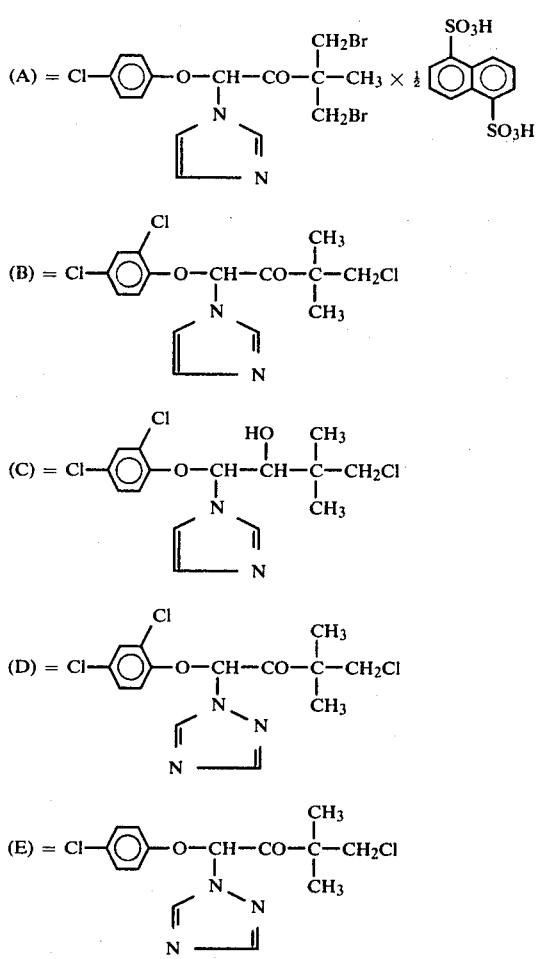

Example 4

Erysiphe test (Barley)/protective/

Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of Erysiphe graminis f.sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (1), (2), (3), (7), (8) and (6).

Example 5

Powdery mildew of barley test (*Erysiphe graminis* var. hordei)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had unfolded their first leaf, they were dusted with fresh spores of *Erysiphe graminis* var. hordei and grown on at 21° to 22° C. and 80 to 90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

In this test, a clearly superior activity compared with the prior art was shown, for example, by the compounds (1), (5), (3), (7), (8) and (6).

Example 6

Erysiphe test (cucumbers)/protective

Solvent: 4.7 parts by weight of acetone
Emulsifier: 0.3 part by weight of alkylaryl polyglycol ether
Water: 95.0 parts by weight The amount of the active compound required for the desired concentration of active compound in the spray liquid was mixed with the stated amount of solvent and the concentrate was diluted with the stated amount of water which contains the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23° to 24° C. and at a relative atmospheric humidity of about 75%.

After 12 days, the infection of the cucumber plants was determined. The assessment data were converted to percent infection. 0% denoted no infection and 100% denoted that the plants were totally infected.

In this test, for example, the following compound showed a very good action which is superior to that of the compound (A) known from the prior art: compound (1).

Example 7

Podosphaera test (apple)/protective

Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contains the stated additions.

Young apple seedlings in the 4 to 6 leaf stage were sprayed with the spray liquid until dripping wet. The plants remained in a greenhouse for 24 hours at 20° C. and at a relative atmospheric humidity f 70%. They were then inoculated by dusting with conidia of the apple powdery mildew causative organism (*Podosphaera leucotricha*) and placed in a greenhouse at a temperature of 21° to 23° C. and at a relative atmospheric humidity of about 70%.

10 days after the inoculation, the infection of the seedlings was determined. The assessment data were converted to percent infection. 0% denoted no infection and 100% denoted that the plants were totally infected.

In this test, for example, the following compounds showed a very good action which was clearly superior to that of the compound (A) known from the prior art: compounds (1) and (2).

It will be apppreciated that the instant specification and examples are set forth by way of illustration and not limitation, and that various modifications and changes may be made without departing from the spirit and scope of the present invention.

We claim:

1. A 4-fluoro-1-azolyl-1-phenoxy-butan-2-one- or -ol of the formula

![structure]

in which
Az is an imidazol-1-yl or 1,2,4-triazol-1-yl radical,
B is a keto or CH(OH) group, and
Y is a methoxy or trifluoromethyl radical,
or an addition product thereof with a physiologically acceptable acid or a metal salt.

2. A compound according to claim 1, which is an addition product with a physiologically acceptable hydrogen halide acid, phosphoric acid, nitric acid, sulphuric acid, a monofunctional or bifunctional carboxylic acid or hydroxycarboxylic acid or a sulphonic acid or with a metal salt in which the metal is copper, zinc, manganese, magnesium, tin, iron and nickel and the anion is derived from hydrochloric, hydrobromic, phosphoric, nitric or sulphuric acid.

3. A compound or addition product thereof according to claim 1, wherein such compound is 3,3-bis-fluoromethyl-1-(imidazol-1-yl)-1-(3-trifluoromethyl-phenoxy)-butan-2-one of the formula ![structure]

4. A compound or addition product thereof according to claim 1, wherein such compound is 3,3-bis-fluoromethyl-1-(1,2,4-triazol-1-yl)-1-(3-trifluoromethyl-phenoxy)-butan-2-one of the formula ![structure]

5. A compound or addition product thereof according to claim 1, wherein such compound is 3,3-bis-fluoromethyl-1-(1,2,4-triazol-1-yl)-1-(4-methoxy-phenoxy)-butan-2-one of the formula ![structure]

6. A compound or addition product thereof according to claim 1, wherein such compound is 3,3-bis-fluoromethyl-1-(1,2,4-triazol-1-yl)-1-(3-trifluoromethyl-phenoxy)-butan-2-ol of the formula ![structure]

7. A compound or addition product thereof according to claim 1, wherein such compound is 3,3-bis-fluoromethyl-1-(1,2,4-triazol-1-yl)-4-(methoxy-phenoxy)-butan-2-ol of the formula ![structure]

8. A fungicidal composition comprising a fungicidally effective amount of a compound or addition product according to claim 1 in admixture with a diluent.

9. A method of combating fungi comprising applying to the fungi, or to a habitat thereof, a fungicidally effective amount of a compound or addition product according to claim 1.

10. The method according to claim 9, wherein the material applied is 3,3-bisfluoromethyl-1-(imidazol-1-yl)-1-(3-trifluoromethylphenoxy)-butan-2-one, 3,3-bisfluoromethyl-1-(1,2,4-triazol-1-yl)-1-(3-trifluoromethyl-1-phenoxy)-butan-2-one, 3,3-bisfluoromethyl-1-(1,2,4-triazol-1-yl)-1-(4-methoxyphenoxy)-butan-2-one, 3,3-bis-fluoromethyl-1-(1,3,4-triazol-1-yl)-1-(3-trifluoromethyl-phenoxy)-butan-2-ol or 3,3-bisfluoromethyl-1-(1,2,4-triazol-1-yl)-1-(4-methoxyphenoxy)-butan-2-ol, or an addition product thereof with a physiologically acceptable acid or a metal salt.

* * * * *